United States Patent [19]

Frisch et al.

[11] Patent Number: 5,869,423
[45] Date of Patent: Feb. 9, 1999

[54] OIL-IN-WATER EMULSIONS

[75] Inventors: Gerhard Frisch, Wehrheim; Zoltan Damo, Eppstein, both of Germany

[73] Assignee: Hoechst Aktiengesellschaft, Frankfurt, Germany

[21] Appl. No.: 669,478

[22] PCT Filed: Dec. 14, 1994

[86] PCT No.: PCT/EP94/04142

§ 371 Date: Sep. 5, 1996

§ 102(e) Date: Sep. 5, 1996

[87] PCT Pub. No.: WO95/17088

PCT Pub. Date: Jun. 29, 1995

[30] Foreign Application Priority Data

Dec. 22, 1993 [DE] Germany ............... 43 43 857.1

[51] Int. Cl.⁶ ............... A01N 25/02; A01N 25/30; B01J 13/00
[52] U.S. Cl. ............... 504/116; 71/DIG. 1; 252/312; 424/405; 514/941; 514/975
[58] Field of Search ............... 252/312; 71/DIG. 1; 424/405; 558/70, 114; 504/116, 194; 514/941, 975

[56] References Cited

U.S. PATENT DOCUMENTS

| | | |
|---|---|---|
| 3,004,056 | 10/1961 | Nunn, Jr. et al. ............... 558/114 |
| 3,740,201 | 6/1973 | Woodruff . |
| 4,174,960 | 11/1979 | Hendriksen ............... 71/DIG. 1 |
| 4,313,847 | 2/1982 | Chasin et al. ............... 252/357 X |
| 4,770,694 | 9/1988 | Iwasaki et al. ............... 71/DIG. 1 |
| 4,870,103 | 9/1989 | Röchling et al. ............... 514/521 |
| 4,966,621 | 10/1990 | Heinrich et al. ............... 504/317 |
| 5,227,402 | 7/1993 | Röchling et al. ............... 514/521 |
| 5,360,783 | 11/1994 | Itoh et al. ............... 504/305 |
| 5,444,078 | 8/1995 | Yu et al. ............... 514/941 X |
| 5,518,991 | 5/1996 | Frisch et al. ............... 504/138 |

FOREIGN PATENT DOCUMENTS

| | | |
|---|---|---|
| 0224846 | 10/1990 | European Pat. Off. . |
| 0118759 | 5/1991 | European Pat. Off. . |
| 3624910 | 1/1988 | Germany . |

*Primary Examiner*—Richard D. Lovering
*Attorney, Agent, or Firm*—Scott E. Hanf

[57] ABSTRACT

The present invention relates to oil-in-water emulsions containing 0.001 to 70% by weight of at least one active substance from the group consisting of phosphates, thiophosphates and/or carbamates, 0.001 to 30% by weight of one or more surfactant compounds from the group consisting of ethoxylated fatty amines or of phosphorylated fatty amine ethoxylates, and also, if desired, adjuvants and water to make up 100% by weight.

16 Claims, No Drawings

OIL-IN-WATER EMULSIONS

Numerous aqueous emulsions of agrochemical active substances have already been disclosed. Such formulations can be prepared, for example, by dissolving the active substances, which are generally insoluble in- water, in organic solvents and adding emulsifiers and adjuvants, the active substances, emulsifiers and adjuvants being added in quantities such that sufficiently stable emulsions are formed when the compositions are formulated with water to the application concentrations.

The prior art has disclosed oil-in-water emulsions which contain phosphorylated surfactants.

EP-A-0 224 846 describes plant protection agents based on aqueous emulsions which contain the active substance and, as dispersant, an alpha- and omega-phosphorylated ethylene oxide/propylene oxide/ethylene oxide block copolymer or a salt thereof.

A disadvantage of the emulsions described is that they are only substantially free of water-immiscible organic solvents.

EP-A-0 118 759 discloses plant protection agents in the form of aqueous emulsion concentrates which contain one or more liquid or dissolved active substances, water and, as oil- and water-soluble dispersants, from 0.5 to 20% by weight of salts of phosphorylated block copolymers based on propylene oxide and ethylene oxide, of the formula

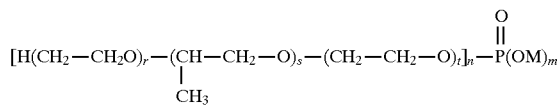

in which
  r and s independently of one another are a number between 20 and 300,
  t is a number between 10 and 300,
  n and m independently of one another are 1 or 2, the sum n+m necessarily being 3, and
  M is an alkali metal cation, one equivalent of an alkaline earth metal cation, ammonium, alkylammonium or alkanolammonium.

The only active substances which are mentioned as being suitable are hydrolysis-resistant insecticides, herbicides and pheromones.

U.S. Pat. No. 4,107,302 relates to aqueous insecticide concentrate mixtures which contain an active substance from the group consisting of phosphates and/or thiophosphates, and a surface-active compound. As nonionic surface-active compounds, ethoxylated alkylallylphenyl ethers are preferably employed, for example distyrylmethylphenol ethoxylate with 10 EO. A disadvantage of the mixtures described therein is the need to use an aqueous buffer solution in order to establish a pH range of from 3.0 to 8.5. Moreover, the addition of organic solvents such as ketones, ethers and alcohols is recommended for mixtures whose content of active substance exceeds 30% by weight.

EP-A-0 196 469 relates to phosphate-containing macroemulsions where the surfactant employed to disperse the active substance is the aqueous solution of a nonylphenol-propylene oxide-ethylene oxide adduct and/or the aqueous solution of an ethylene oxide/propylene oxide/ethylene oxide block copolymer having an average molecular weight of between 2000 and 8000 and HLB values of between 8 and 30. The macroemulsions described necessarily contain glycerol as adjuvant. When employing an active substance which is solid at room temperature, a solution of the substance concerned in an aromatic diluent is used.

EP-A-0 130 370 relates to plant protection agent combinations which are obtained by mixing a dispersion of active substance and a solution of active substance. The plant protection agent combinations prepared in this way contain as phosphorylated surfactants, for example, the Na salt of $C_{12}$–$C_{18}$-alkyl polyglycol ether phosphate mono/diester (®Forlanit P, Henkel KGaA) and triethanolamide salts of a mixture of mono- and diphosylates of a tri-styrylphenol polyglycol ether having 18 EO units (®Soprophor FI, Rhone-Poulenc) and, as sulfated and sulfonated surfactant compounds, for example, the Na salt of the sulfosuccinic monoester and Na ligninsulfonate. A disadvantage of the plant protection agent combinations described therein is the use of solutions of active substances, which have a high content (from 40 to 48% by weight) of organic solvents such as xylene and methylnaphthalene.

Oil-in-water emulsions which contain nonionic surfactants as dispersants are likewise known from the prior art.

EP-A-0 289 909 relates to stable aqueous emulsions of organophosphorus pesticides which in addition to the active substance contain a nonionic block copolymer, copolymer or coblock copolymer as surfactant and also, necessarily, urea, so as to achieve an adequate degree of phase stabilization.

The object of the present invention was to provide plant protection formulations, in the form of aqueous emulsion concentrates based on active substances, especially of active substances which are sensitive to hydrolysis, from the group consisting of phosphates, thiophosphates and/or carbamates, which formulations are completely free from organic solvents, have an excellent chemical and physical stability, are resistant in particular to hydrolysis, and are also stable at low temperatures (–10° C.), and which are dilutable with water as desired either alone or in a mixture with other liquid formulations.

It has now surprisingly been found that the use of specific surfactant compounds leads to the desired plant protection formulations. Specifically, these surfactant compounds are
  A) fatty amine ethoxylates of the formula I and
  B) phosphorylated fatty amine ethoxylates of the formula II.

The present invention relates to oil-in-water emulsions comprising:
0.001 to 70% by weight, preferably 0.5 to 50% by weight, of at least one active substance from the group consisting of phosphates, thiophosphates and/or carbamates,
0.001 to 30% by weight, preferably 0.1 to 20% by weight, of one or more surfactant compounds from the group consisting of
  A) ethoxylated fatty amines of the formula I

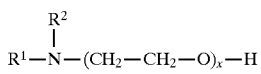

in which
  $R^1$ is hydrogen
  $C_1$–$C_{24}$-alkyl,
  $C_2$–$C_{24}$-alkenyl,
  $C_2$–$C_{24}$-alkynyl,
  $C_5$–$C_{24}$-cycloalkyl,
  $C_6$–$C_{36}$-aryl,
  $C_6$–$C_{48}$-alkaryl,
  $C_6$–$C_{36}$-heteroaryl or
  $C_6$–$C_{48}$-heteroalkaryl, $R^2$ is $R^1$, with the exception of hydrogen, or is a group of the formula $(CH_2\text{—}CH_2\text{—}O)_y\text{—}H$ and x, y independently of one another are a number between 1 and 200 or

B) phosphorlated fatty amine ethoxylates of the formula II

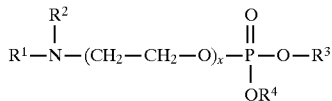

in which $R^1$ is hydrogen
$C_1$–$C_{24}$-alkyl,
$C_2$–$C_{24}$-alkenyl,
$C_2$–$C_{24}$-alkynyl,
$C_5$–$C_{24}$-cycloalkyl,
$C_6$–$C_{36}$-aryl,
$C_6$–$C_{48}$-alkaryl,
$C_6$–$C_{36}$-heteroaryl or
$C_6$–$C_{48}$-heteroalkaryl, R is $R^1$, with the exception of hydrogen, or is a group of the formula

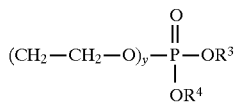

$R^3$, $R^4$ independently of one another are hydrogen, an alkali metal cation, one equivalent of an alkaline earth metal ion,
ammonium,
mono-, di- or tri($C_1$–$C_{12}$-alkyl)ammonium or
mono-, di- or tri($C_1$–$C_{12}$-alkanol)ammonium, and x, y independently of one another are a number between 1 and 200 and, if desired, adjuvants and water to make up 100% by weight.

The O/W emulsions according to the invention contain at least one agrochemical active substance, an active substance for controlling harmful organisms in the household and hygiene sector and/or a pharmacologically active substance from the class of the phosphates, thiophosphates and/or carbamates. In this context the active substances, preferably active substances sensitive to hydrolysis, which are suitable include both those substances which are liquid at room temperature and those which are solid at room temperature. Such active substances are known and described, for example, in "The Pesticide Manual" 9th edition, The British Crop. Protection Council, 1991.

In the present case the term agrochemical substances is understood to refer to those substances which are usually employed in plant protection. Examples of these include insecticides, acaricides, fungicides, nematicides, herbicides, molluscicides, rodenticides, growth regulators, safeners, adjuvants, fertilizers and algicides.

Specific examples of such active substances are:
O,O-diethyl O-[2-isopropyl-4-methyl-6-pyrimidyl] thiophosphate (diazinon)
O,O-diethyl O-[3,5,6-trichloro-2-pyridyl]thiophosphate (chlorpyrophos)
2-(1-methylpropyl)phenyl methyl carbamate (BPMC)
O,O-dimethyl S-methylcarbamoylmethyl thiophosphate (dimethoate)
chlorobicyclo[3.2.0]hepta-2,6-diene-6-yl phosphate (heptenophos)
O,O-diethyl O-1-phenyl-1H-1,2,4-triazol-3-yl thiophosphate (triazophos)
ethyl 2-diethoxyphosphinothioyloxy-5-methylpyrazolyl[1,5-α]pyrimidine-6-carboxylate (pyrazophos)
O,O-diethyl O-(4-nitrophenyl) thionophosphate
O,O-dimethyl O-(4-nitrophenyl) thionophosphate (fenitrothion)
O-ethyl O-4-methylthiophenyl S-propyl dithiophosphate
2-isopropoxyphenyl N-methylcarbamate
2,3-dihydro-2,2-dimethyl-7-benzofuryl methylcarbamate
3,5-dimethyl-4-methylthiophenyl N-methylcarbamate
O,O-diethyl O-(3-chloro-4-methyl-7-coumarinyl) thibphosphate
S-[1,2-bis (ethoxycarbonyl) ethyl] O,O-dimethyl dithiophosphate (malathion)
O,O-dimethyl O-4-methylmercapto-3-methylphenyl thionophosphate (fenthion, Lebaycid)
O-ethyl O-2-isopropyloxycarbonylphenyl N-isopropylthionophosphoramide.

In the present case, active substances for controlling pests in the household and hygiene sector are to be understood as all conventional active substances of low solubility in water. Specific examples of such active substances are:
2-isopropoxyphenyl N-methylcarbamate
O,O-diethyl O-4-nitrophenyl thionophosphate (ethylparathion)
O,O-dimethyl O-4-nitrophenyl thionophosphate (methylparathion)
S-[1,2-bis (ethoxycarbonyl) ethyl] O,O-dimethyl dithiophosphate
O,O-dimethyl O-3-methyl-4-nitrophenyl thionophosphate (sumithion, folithion)
O,O-dimethyl O-4-methylmercapto-3-methylphenyl thionophosphate (Lebaycid, fenthion).

In the present case pharmacologically active substances are to be understood as substances of low solubility in water which can be preferably employed in the veterinary sector. An example of such active substances is chlorobicyclo [3.2.0]hepta-2,6-dien-6-ylphosphate (heptenophos).

The formulations according to the invention contain at least one compound of the formula I or II.

In the compounds of the formula I $R^1$ is preferably hydrogen, $C_{10}$–$C_{18}$-alkyl, $C_2$–$C_{18}$-alkenyl, $C_6$–$C_{20}$-cycloalkyl, $C_6$–$C_{18}$-aryl or ($C_1$–$C_{12}$-alkyl)$_3$-phenyl, especially $C_1$–$C_{12}$-alkylphenyl or mono-, di- or tristyrylphenyl.

$R^2$ is preferably $C_{10}$–$C_{18}$-alkyl, $C_2$–$C_{18}$-alkenyl, $C_6$–$C_{20}$-cycloalkyl, $C_6$–$C_{18}$-aryl, ($C_1$–$C_{12}$-alkyl)$_3$-phenyl, and in particular $C_1$–$C_{12}$-phenyl, mono-, di- or tristyrylphenyl or a group of the formula $(CH_2\text{—}CH_2\text{—}O)_y\text{—}H$ in which y is a number between 1 and 120.

Since the amines which are employed in the synthesis of the compounds of the formula. I, especially in the case of fatty amines in which $R^1$ and/or $R^2$ are alkyl and/or alkenyl groups, generally represent random mixtures of homologs and isomers, it is advantageous to talk of an average number of carbon atoms for these radicals $R^1$ and $R^2$.

Where they are not hydrogen, the radicals $R^1$ and $R^2$ may carry suitable substituents, examples being halogen atoms, alkoxy group, hydroxyl group, nitro group, amino group and/or carboxyl ester group.

The indices x and y indicate the number of moles of ethylene oxide units. The preferred ranges for x and y are between 1 and 120, between 1 and 80 and between 1 and 30.

Quite particularly suitable fatty amine ethoxylates of the formula I are coconut fatty amine ethoxylates, oleylamine ethoxylates, stearylamine ethoxylates and tallow fatty amine ethoxylates in which x is a number between 1 and 40 and the corresponding bisethoxylates thereof in which x and y independently of one another are a number between 1 and 40.

The surfactants of the formula I can be prepared in a simple manner. Usually these compounds are prepared by ethoxylation of the amines on which they are based (see K. Kosswig and H. Stache, "Die Tenside" [The Surfactants], Hauser-Verlag, p. 157).

For the compounds of the formula II $R^1$ is preferably $C_{10}$–$C_{18}$-alkyl, $C_2$–$C_{18}$-alkenyl, $C_6$–$C_{20}$-aryl, $C_1$–$C_{12}$-alkylphenyl, or mono-, di- or tristyrylphenyl.

$R^2$ is preferably $C_{10}$–$C_{18}$-alkyl, $C_2$–$C_{18}$-alkenyl, $C_6$–$C_{20}$-aryl, $C_1$–$C_{12}$-alkylphenyl, mono-, di- or tristyrylphenyl or a group of the formula

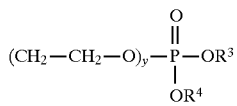

in which y, $R^3$ and $R^4$ have the preferred meanings indicated below.

Since the amines which are employed in the synthesis of the compounds of the formula II, especially in the case of fatty amines in which $R^1$ and/or $R^2$ are alkyl and/or alkenyl groups, generally represent random mixtures of homologs and isomers, it is advantageous to talk of an average number of carbon atoms for these radicals $R^1$ and $R^2$.

Where the radicals $R^1$ and $R^2$ are other than hydrogen, they may carry suitable substituents, examples being halogen atoms, alkoxy groups, hydroxyl groups, nitro groups, amino groups and/or carboxyl ester groups.

For the indices x and y the preferred ranges are between 1 and 120, between 1 and 80 and between 1 and 30. $R^3$ and $R^4$ independently of one another are preferably hydrogen, an alkali metal ion, mono-, di- or tri($C_2$–$C_4$-alkyl)ammonium or tri($C_2$–$C_4$-alkanol)ammonium.

The surfactants of the formula II can be prepared in a simple manner. Usually these compounds are produced by reaction of the amine ethoxylates on which they are based with polyphosphoric acid or phosphorus pentoxide (see K. Kosswig, loc. cit., p. 133).

The O/W emulsions according to the invention contain water as continuous phase. In the case of concentrated emulsions the proportion of water is relatively low, whereas the emulsions in the diluted state contain relatively large quantities of water. The oil phase (=disperse phase) is present in the form of finely divided droplets in the aqueous phase, the droplet size being variable within a certain range. The particle diameter is generally between 0.001 and 10 $\mu$m, preferably between 0.01 and 5 $\mu$m.

These O/W emulsions advantageously contain no organic solvents. Therefore they have a high flash point, are of low flammability and are virtually odorless.

Adjuvants which may be present in the oil-in-water emulsions according to the invention are preservatives, low temperature stabilizers, dyes and odor improvers. Examples of preservatives are 2-hydroxybiphenyl, sorbic acid, p-hydroxybenzaldehyde, methyl p-hydroxybenzoate, benzaldehyde, benzoic acid, propyl p-hydroxybenzoate and p-nitrophenol. The content of preservative in the emulsion may be between 0.01 and 1% by weight.

Suitable low temperature stabilizers are glycol, glycerol, polyethylene glycol, sugars and salts such as ammonium sulfate and sodium oleate, the emulsions usually being able to have a content of from 1 to 10% by weight. Examples of dyes are azo dyes and phthalocyanine dyes. Odor improvers which it is possible to employ are perfume oils.

One example of a suitable preparation process for these O/W emulsions is described in EP-B-0 130 370. In principle, however, the two phases can be brought into the desired state by stirring.

The oil-in-water emulsions are distinguished by the fact that they are stable under the conditions prevailing in practice. On long-term storage these emulsions remain unchanged with regard to their physical stability and their content of active substance both at high temperatures (50° C.) and at low temperatures (−5° C., −10° C.). A further advantage is that active substances which are solid or liquid at room temperature can be emulsified with equal success. The mandatory addition of glycerol and of organic solvents, especially when solid active substances are employed (cf. EP-A-0 196 463), is not required.

The oil-in-water emulsions according to the invention can be applied either as prepared or after dilution beforehand. In this context their application depends on the concentration of the oil-in-water emulsion and on the particular indication. The emulsion is applied by the conventional methods and thus, for example, by spraying or pouring. In the application of the oil-in-water emulsions according to the invention an excellent activity was found with regard to harmful organisms such as aphids, grain weevils, mealy-bugs and bean weevils. In this context it should be mentioned that no phytotoxicity was detected, especially in relation to dwarf beans, field beans, tomatoes, cucumbers, wild apple stock and vines.

EXAMPLES

Plant Protection Formulations With Surfactant of the Formula I

Table I shows oil-in-water emulsions according to the invention which contain as surfactant compound a bisethoxylated tallow-fatty amine ($R^1$=$C_{14}$ (5%), $C_{16}$ (30%), $C_{18}$ (65%)., x=7, y=8).

The emulsions indicated are stable on storage for a period of at least one month (storage temperature: 25° C., 50° C.).

TABLE I

| Data in % by weight, water to make up to 100% by weight | | | | | | | |
|---|---|---|---|---|---|---|---|
| Example | 1 | 2 | 3 | 4 | 5 | 6 | 7 |
| Surfactant | 7.0 | 7.0 | 6.0 | 7.0 | 8.5 | 5 | 7.0 |
| Malathion | 42.0 | 40.0 | 35.0 | 42 | 42 | 30 | 42 |
| Lactic acid | 0.35 | 0.34 | 0.3 | 0.35 | 0.42 | 0.25 | 0.35 |
| Kelzan, 2% in $H_2O$ | 13.3 | 13.3 | 13.3 | 9.4 | 10.0 | 18.0 | 2.0 |

Plant Protection Formulations With Surfactant of the Formula II

Table II shows oil-in-water emulsions according to the invention which contain a phosphorylated fatty amine bisethoxylate of the formula II in which $R^1$ is $C_{14}$ (5%), $C_{16}$ (30%), $C_{18}$ (65%)

$R^2$ is a group of the formula

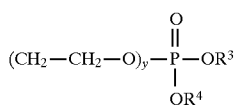

in which
$R^3$ and $R^4$ are hydrogen,
x is the number 7 and
y is the number 8.

Data in % by weight, water to make up to 100% by weight

| Example | 1 | 2 | 3 | 4 | 5 |
|---|---|---|---|---|---|
| Malathion | 42.0 | 42.0 | 35.0 | 25.0 | 40.0 |
| Surfactant 1 | 7.0 | 8.0 | 6.0 | 9.0 | 11.0 |
| Kelzan, 2% in $H_2O$ | 13.3 | 15.0 | 10.8 | 20.0 | 17.0 |
| Triethanolamine | 3.6 | 4.0 | 3.1 | 4.7 | 5.9 |

We claim:

1. An oil-in-water emulsion which contains one or more active substances and one surfactant compound, consisting essentially of:
   0.001 to 70% by weight, of at least one active substance from the group consisting of phosphates, thiophoshates, carbamates, and mixtures thereof, 0.001 to 30% by weight, of one surfactant compound from the group consisting of
   A) ethoxylated fatty amines of formula I

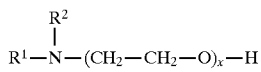

in which
   $R^1$ is hydrogen
      $C_1$–$C_{24}$-alkyl,
      $C_2$–$C_{24}$-alkenyl,
      $C_2$–$C_{24}$-alkynyl,
      $C_5$–$C_{24}$-cycloalkyl,
      $C_6$–$C_{36}$-aryl,
      $C_6$–$C_{48}$-alkaryl,
      $C_6$–$C_{36}$-heteroaryl or
      $C_6$–$C_{48}$-heteroalkaryl,
   $R_2$ is $R^1$, with the exception of hydrogen, or is a group of the formula $(CH_2\text{—}CH_2\text{—}O)_y\text{—}H$
   and
   x, y independently of one another are a number between 1 and 200 and
   B) phosphorylated fatty amine ethoxylates of the formula II

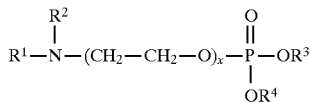

in which
   $R^1$ is hydrogen
      $C_1$–$C_{24}$-alkyl,
      $C_2$–$C_{24}$-alkenyl,
      $C_2$–$C_{24}$-alkynyl,
      $C_5$–$C_{24}$-cycloalkyl,
      $C_6$–$C_{36}$-aryl,
      $C_6$–$C_{48}$-alkaryl,
      $C_6$–$C_{36}$-heteroaryl or
      $C_6$–$C_{48}$-heteroalkaryl,
   $R^2$ is $R^1$, with the exception of hydrogen, or is a group of the formula

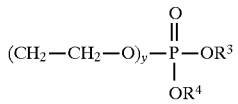

$R^3$, $R^4$ independently of one another are hydrogen, an alkali metal cation, one equivalent of an alkaline earth metal ion, ammonium, mono-, di- or tri($C_1$–$C_{12}$-alkyl) ammonium or mono-, di- or tri($C_1$–$C_{12}$-alkanol) ammonium, and
   x, y independently of one another are a number between 1 and 200, but not both groups A) and B) and, optionally adjuvants and water to make up 100% by weight.

2. An oil-in-water emulsion as claimed in claim 1, wherein in the surfactant compound of the formula I
$R^1$ is hydrogen, $C_{10}$–$C_{18}$-alkyl, $C_2$–$C_{18}$-alkenyl, $C_6$–$C_{20}$-cycloalkyl, $C_6$–$C_{18}$-aryl, or $(C_1$–$C_{12})_3$-phenyl.

3. An oil-in-water emulsion as claimed in claim 1, wherein
$R^2$ is $C_1$–$C_{10}$-alkyl, $C_2$–$C_{18}$-alkenyl, $C_6$–$C_{20}$-cycloalkyl, $C_6$–$C_{18}$-aryl, $(C_1$–$C_{12}$-alkyl)$_3$-phenyl, $C_1$–$C_{12}$-alkylphenyl, mono-, di- or tristyrylphenyl or a group of the formula $(CH_2\text{—}CH_2\text{—}O)_y\text{—}H$ in which y is a number between 1 and 120.

4. An oil-in-water emulsion as claimed in claim 1, wherein in the surfactant compounds of the formula I x and y independently of one another are a number between 1 and 120.

5. An oil-in-water emulsion as claimed in claim 1, wherein in the surfactant compounds of the formula II
$R^1$ is $C_{10}$–$C_{18}$-alkyl, $C_2$–$C_{10}$-alkenyl, $C_6$–$C_{20}$-aryl, $C_1$–$C_{12}$-alkylphenyl or mono-, di- or tristyrylphenyl.

6. An oil-in-water emulsion as claimed in claim 1, wherein in the surfactant compounds of the formula II
R is $C_{10}$–$C_{18}$-alkyl, $C_2$–$C_{18}$-alkenyl, $C_6$–$C_{20}$-aryl, $C_1$–$C_{12}$-alkylphenyl, mono-, di- or tristyrylphenyl or a group of the formula

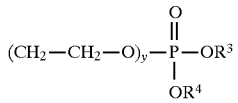

in which $R^3$ and $R^4$ independently of one another are hydrogen, an alkali metal ion, mono-, di- or tri($C_2$–$C_4$-alkyl)ammonium or tri($C_2$–$C_4$-alkanol)ammonium and y is a number between 1 and 120.

7. An oil-in-water emulsion as claimed in claim 1, wherein x and y independently of one another are a number between 1 and 120.

8. An oil-in-water emulsion as claimed in claim 1, which comprises as adjuvants preservatives, low temperature stabilizers, dyes and/or odor improvers.

9. An oil-in-water emulsion as claimed in claim 1, wherein the oil phase is present in the form of finely divided droplets in the aqueous phase.

10. An oil-in-water emulsion as claimed in claim 1, wherein the particle diameter of the droplets is between 0.001 and 10 $\mu m$.

11. An oil-in-water emulsion as claimed in claim 1, wherein said emulsion is essentially free of any organic solvent.

12. A method of protecting plants comprising the step of applying to the plants the oil-in-water emulsion as claimed in claim 1.

13. A method as claimed in claim 12, wherein said method assists in the control of organisms harmful to the plants.

14. An oil-in-water emulsion which contains one or more active substances and one surfactant compound, and comprises 0.001 to 70% by weight, of at least one active substance from the group consisting of phosphates, thiophoshates, carbamates, and mixtures thereof, 0.001 to 30% by weight, of one surfactant compound from the group consisting of A) ethoxylated fatty amines of formula I

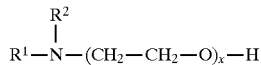

in which
$R^1$ is hydrogen
$C_1$–$C_{24}$-alkyl,
$C_2$–$C_{24}$-alkenyl,
$C_2$–$C_{24}$-alkynyl,
$C_5$–$C_{24}$-cycloalkyl,
$C_6$–$C_{36}$-aryl,
$C_6$–$C_{48}$-alkaryl,
$C_6$–$C_{36}$-heteroaryl or
$C_6$–$C_{48}$-heteroalkaryl, $R^2$ is $R^1$, with the exception of hydrogen, or is a group of the formula $(CH_2$—$C_2$—$O)_y$—$H$
and x, y independently of one another are a number between 1 and 200 and B) phosphorylated fatty amine ethoxylates of the formula II

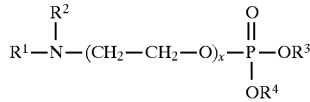

in which
$R^1$ is hydrogen
$C_1$–$C_{24}$-alkyl,
$C_2$–$C_{24}$-alkenyl,
$C_2$–$C_{24}$-alkynyl,
$C_5$–$C_{24}$-cycloalkyl,
$C_6$–$C_{36}$-aryl,
$C_6$–$C_{48}$-alkaryl,
$C_6$–$C_{36}$-heteroaryl or
$C_6$–$C_{48}$-heteroalkaryl, $R^2$ is $R^1$, with the exception of hydrogen, or is a group of the formula

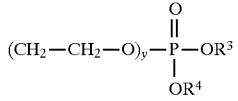

$R^3$, $R^4$ independently of one another are hydrogen, an alkali metal cation, one equivalent of an alkaline earth metal ion, ammonium, mono-, di- or tri($C_1$–$C_{12}$-alkyl) ammonium or mono-, di- or tri($C_1$–$C_{12}$-alkanol) ammonium, and x, y independently of one another are a number between 1 and 200, but not both groups A) and B) and, optionally adjuvants and water to make up 100% by weight wherein:
the amount of said active substance is 0.5 to 50% by weight, and the amount of said surfactant compound is 0.1 to 20% by weight;

in said surfactant compound of formula I, $R^1$ is $C_1$–$C_{12}$-phenyl or mono-, di- or tri-styrylphenyl, and x and y, independently of one another, are numbers between 1 and 80; and the oil phase is present in the form of finely divided droplets in the aqueous phase, said droplets having a particle diameter between 0.01 and 5 μm.

15. An oil-in-water emulsion as claimed in claim 14, wherein x and y, independently of one another, are numbers between 1 and 30, and wherein said particle diameter is between 0.1 and 2 μm.

16. An oil-in-water emulsion as claimed in claim 14, wherein at least one said active substance is active in the control of harmful organisms and is sensitive to hydrolysis.

* * * * *